United States Patent [19]
Johnson et al.

[11] Patent Number: 5,770,191
[45] Date of Patent: Jun. 23, 1998

[54] ACTIVE C-TERMINAL PEPTIDES OF INTERFERON—GAMMA AND THEIR USE

[75] Inventors: Howard M. Johnson; Brian E. Szente, both of Gainesville, Fla.

[73] Assignee: University of Florida, Gainesville, Fla.

[21] Appl. No.: 449,639

[22] Filed: May 24, 1995

[51] Int. Cl.⁶ .............................. A61K 38/21; C07K 14/57
[52] U.S. Cl. ......................... 424/85.5; 530/351; 530/324; 514/12; 424/450
[58] Field of Search ................................. 424/85.5, 450; 514/12; 530/351, 324

[56] References Cited

U.S. PATENT DOCUMENTS

| | | | |
|---|---|---|---|
| 4,908,432 | 3/1990 | Yip | 530/351 |
| 5,235,038 | 8/1993 | Blondelle et al. | 530/324 |

FOREIGN PATENT DOCUMENTS

92/06115   4/1992   WIPO.

OTHER PUBLICATIONS

Fairchild, R.L., J.W. Moorhead (1985) "A Simple and Sensitive ELISA to Detect Immune (?) Interferon Induced I–A on a Macrophage Line" Journal of Immunological Methods 85:183–193.
Farrar, M.A., R.D. Schreiber (1993) "The Molecular Cell Biology of Interferon–γ and its Receptor" Annu. Rev. Immunol. 11:571–611.
Gray, P.W., D.V. Goeddel (1983) "Cloning and expression of murine immune interferon cDNA" Proc. Natl. Acad. Sci. USA 80:5842–5846.
Griggs, N.D. et al. (1992) "The N–Terminus and C–Terminus of IFN–γ are Binding Domains for Cloned Soluble IFN–γ Receptor" The Journal of Immunology 149(2):517–520.
Johnson, H.M. (1985) "Mechanism of Interferon γ Production and Assessment of Immunoregulartory Properties" Lymphokines 11:33–46.
Leinikki, P.O. et al. (1987) "Reduced Receptor Binding by a Human Interferon–γ Fragment Lacking 11 Carboxyl–Terminal Amino Acids" The Journal of Immunology 139(10):3360–3366.
Lundell, D. et al. (1991) "The carboxyl–terminal region of human interferon γ is important for biological activity: mutagenic and NMR analysis" Protein Engineering 4(3):335–341.
Magazine, H.I. et al. (1988) "Use of synthetic peptides to identify an N–terminal epitope on mouse γ interferon that may be involved in function" Proc. Natl. Acad. Sci. USA 85:1237–1241.
Pestka, S. et al. (1987) "Interferons and their Actions" Ann. Rev. Biochem. 56:727–777.
Rinderknecht, E. et al. (1984) "Natural Human Interferon–γ" The Journal of Biological Chemistry 259(11):6790–6797.
Russell, J.K. et al. (1986) "Epitope and Functional Specificity of Monoclonal Antibodies to Mouse Interferon–γ: The Synthetic Peptide Approach" The Journal of Immunology 136(9):3324–3328.
Sanceau, J. et al. (1987) "Intracellular human γ–interferon triggers an antiviral state in transformed murine L cells" Proc. Natl. Acad. Sci. USA 84:2906–2910.
Seelig, G.F. et al. (1988) "Evidence for a Polypetide SEgment at the Carboxyl Terminus of Recombinant Human γ Interferon Involved in Expression of Biological Activity" Biochemistry 27:1981–1987.
Smith, M.R. et al. (Direct Evidence for an Intracellular Role for IFN–γ The Journal of Immunology 144(5):1777–1782.
Steeg, P.S. et al. (1982) "Regulation of Murine Macrophage Ia Antigen Expression by a Lymphokine with Immune Interferon Activity" Journal of Experimental Medicine 156:1780–1793.
Szente, B.E., H.M. Johnson (1994) "Binding of IFNγ and its C–Terminal Peptide toa Cytoplasmic Domain of its Receptor that is Essential for Function" Biochemical and Biophysical Research Communications 201(1):215–221.
Szente, B.E., H.M. Johnson (1994) "The C–Terminus of IFNγ is Sufficient for Intracellular Function" Biochemical and Biophysical Research Communications 203(3):1645–1654.
VanVolkenburg, M.A. et al. (1993) "Binding Site on the Murine IFN–γ Receptor for IFN–γ Has Been Identified Using the Synthetic Peptide Approach" The Journal of Immunology 151(11):6206–6213.
Weigent, D.A. et al. (1981) "Virus Yield–Reduction Assay for Interferon by Titration of Infectious Virus" Methods in Enzymology 78:346–351.
Wetzel, R. et al. (1990) "Mutational analysis of the C–terminus of human interferon–γ" Protein Engineering 3(7):611–623.
Zlotnik, A. et al. (1983) "Characterization of the γ–Interferon–Mediated Induction of Antigen–Presenting Ability in P388D1 Cells" Journal of Immunology 131(6):2814–2820.
Fidler, I. J. et al. (1985) *J. Immunol.* 135: 4289–96.

*Primary Examiner*—David L. Fitzgerald
*Attorney, Agent, or Firm*—Saliwanchik, Lloyd & Saliwanchik

[57] ABSTRACT

The subject invention concerns novel peptides of gamma interferon (IFNγ) and methods of use of these peptides. Specifically exemplified are peptides from the C-terminus of IFNγ. The subject peptides, once internalized into a cell, have biological activity which is comparable to the full-length IFNγ protein.

19 Claims, 3 Drawing Sheets

ACTIVE C-TERMINAL PEPTIDES OF INTERFERON—GAMMA AND THEIR USE

This invention was made with government support under National Institutes of Health grant number CA 38779. The government has certain rights in the invention.

BACKGROUND OF THE INVENTION

Interferon gamma (IFNγ) is a pleiotropic cytokine product of lymphocytes (subtype Th-1) and natural killer (NK) cells which plays a critical role in a variety of immunological functions (Farrar, M. A. et al., (1993). The cDNA and amino acid sequences for both murine and human IFNγ have been determined (Gray, P. W. et al., 1983); Rinderknecht, E. et al., 1984). Both the murine and human IFNγ proteins exist as homodimers that are biologically active.

Among IFNγ's many effects are the induction of a number of antiviral proteins, upregulation of class II MHC expression, a role in B cell maturation, activation of cells to cytotoxic states, and release of mediators of inflammation (Johnson, H. M., 1985). Thus, IFNγ plays an important role in host defense, inflammation and autoimmunity. These activities are induced as the IFNγ molecule interacts in a species-specific manner with a single class of cell surface receptor and an associated cofactor molecule (Pestka, S. et al., 1987). In both mice and in humans, the IFNγ receptor is a single chain glycoprotein of approximately 85–90 kD which has fairly large (>200 amino acids) extracellular and cytoplasmic domains.

An understanding of the structural basis for IFNγ binding to its receptor provides insight into the mechanism by which ligand binding activates signal transduction. Murine IFNγ has been shown to bind to a soluble form of its receptor via both the N-terminus and the C-terminus of the protein (Russell, J. K. et al., 1986; Magazine, H. I. et al., 1988; Griggs, N. D. et al., 1992). While the N-terminus of murine IFNγ binds to the extracellular domain of the receptor (amino acid residues 95–120 of the receptor) (VanVolkenburg, M. A. et al., 1993), the C-terminus of murine IFNγ does not bind to this region of the receptor. A C-terminal peptide of murine IFNγ, consisting of amino acid residues 95–133, binds to the membrane proximal region of the cytoplasmic domain of the murine IFNγ receptor (amino acid residues 253–287) and human IFNγ receptor (amino acid residues 252–291) (Szente, B. E. et al, 1994(a); Szente, B. E. et al., 1994(b)). Previous studies have shown that intracellular IFNγ can induce an antiviral state and upregulation of MHC class II molecules in a species nonspecific fashion (Sancéau, J. et al., 1987; Smith, M. R. et al., 1990).

Although it has been known that certain deletions or mutations of amino acids in the C-terminus of the IFNγ molecule can diminish the biological activity of the protein, the discovery of peptides that comprise a portion of the C-terminus sequence of the full-length IFNγ and that retain biological activity was unexpected.

BRIEF SUMMARY OF THE INVENTION

The subject invention concerns the discovery that a peptide fragment of human IFNγ, designated as huIFNγ (95–134) (SEQ ID NO. 1), corresponding to amino acid residues 95–134 of mature full-length IFNγ, binds to the cytoplasmic domain of the IFNγ receptor. The subject invention also concerns the murine counterpart, the peptide designated as muIFNγ (95–133) (SEQ ID NO. 2), which also binds to the cytoplasmic domain of the IFNγ receptor. The IFNγ peptides of the subject invention bind to IFNγ receptor protein in a species nonspecific manner.

The subject invention further concerns the discovery that both the huIFNγ (95–134) (SEQ ID NO. 1) and muIFNγ (95–133) (SEQ ID NO. 2) peptides have biological activity similar to the activity observed with full-length IFNγ. Internalization of both murine and human IFNγ C-terminal peptides by mouse macrophage cell lines, independent of the extracellular domain of the IFNγ receptor, results in the induction of an antiviral state, as well as induction of MHC class II expression on the target cell. Thus, the subject invention also concerns the use of the peptides described herein as agonists of IFNγ biological activity. The subject peptides can be used to treat a variety of clinically relevant disease states in animals and humans.

BRIEF DESCRIPTION OF THE SEQUENCES

SEQ ID NO. 1 is an amino acid sequence of an IFNγ peptide designated huIFNγ (95–134).

SEQ ID NO. 2 is an amino acid sequence of an IFNγ peptide designated muIFNγ (95–133).

SEQ ID NO. 3 is an amino acid sequence of a peptide designated muIFNγ (95–133)S. The sequence shown for SEQ ID NO. 3 is a scrambled version of SEQ ID NO. 2.

SEQ ID NO. 4 is an amino acid sequence of an IFNγ peptide designated muIFNγ (95–125).

SEQ ID NO. 5 is an amino acid sequence of an IFNγ peptide designated muIFNγ (1–39).

SEQ ID NO. 6 is a polycationic amino acid sequence present in the C-terminal region of mouse IFNγ.

SEQ ID NO. 7 is a polycationic amino acid sequence present in the C-terminal region of human IFNγ.

SEQ ID NO. 8 is an amino acid sequence of mature, full-length human IFNγ.

SEQ ID NO. 9 is an amino acid sequence of mature, full-length murine IFNγ.

DETAILED DESCRIPTION OF THE INVENTION

The subject invention pertains to agonist peptides of IFNγ. These peptides are based on the amino acid sequence of the C-terminus region of the IFNγ molecule and are capable of binding to the cytoplasmic domain of the IFNγ receptor. Surprisingly, these peptides were found to possess the same or similar biological activity as that associated with the full-length, mature IFNγ protein, even though these peptides do not bind to the extracellular domain of the IFNγ receptor. Specific embodiments of the subject peptides have been shown to effect increased resistance to viral infection, as well as increased expression of MHC class II molecules on the target cell surface. Full-length IFNγ is known to induce resistance to infection and increased MHC class II expressions in target cells.

In a preferred embodiment, the huIFNγ (95–134) peptide (SEQ ID NO. 1) based on human IFNγ has an amino acid sequence corresponding to amino acid residues 95 through 134 of the full-length human IFNγ protein (SEQ ID NO. 8). The muIFNγ (95–133) peptide (SEQ ID NO. 2) based on murine IFNγ has an amino acid sequence corresponding to amino acid residues 95 through 133 of the full-length murine IFNγ protein (SEQ ID NO. 9). These peptides are shown in Table 1, along with the amino acid sequence of the peptides designated muIFNγ (95–133)S (SEQ ID NO. 3), muIFNγ (95–125) (SEQ ID NO. 4), and muIFNγ (1–39) (SEQ ID NO. 5). The muIFNγ (95–133)S (SEQ ID NO. 3) peptide is a scrambled version of the muIFNγ (95–133) (SEQ ID NO. 2) peptide. The muIFNγ (1–39) (SEQ ID NO. 5) and muIFNγ (95–125) (SEQ ID NO. 4) have an amino acid sequence corresponding to amino acid residues 1 through 39 and 95 through 125 of the full-length murine IFNγ protein (SEQ ID NO. 9), respectively.

TABLE 1

Sequence of murine and human IFNγ peptides

| PEPTIDE | SEQUENCE |
| --- | --- |
| huIFNγ(95-134) | SEQ ID NO. 1: LTNYSVTDLNVQRKAIHELIQVMAELSPAAKTGKRKRSQM |
| muIFNγ(95-133) | SEQ ID NO. 2: AKFEVNNPQVQRQAFNELIRVVHQLLPESSLRKRKRSRC |
| muIFNγ(95-133)S* | SEQ ID NO. 3: PSCRENQNAVKIQKLSVVLRREQKHRVERLAFRNQSLPF |
| muIFNγ(95-125) | SEQ ID NO. 4: AKFEVNNPQVQRQAFNELIRVVHQLLPESSL |
| muIFNγ(1-39) | SEQ ID NO. 5: HGTVIESLESLNNYFNSSGIDVEEKSLFLDIWRNWQKDG |

The peptides shown in Table 1 were tested for their ability to increase viral resistance in a murine macrophage cell line, P388D$_1$, using a standard viral yield reduction assay. In order to get the peptides internalized within the cytoplasm of a cell, macrophage cell lines were used because of their ability to nonspecifically endocytose material. The murine macrophage line P388D$_1$ is known to be actively phagocytic/endocytic, and also responds well to IFNγ treatment (Zlotnik, A. et al., 1983; Fairchild, R. L. et al., 1985; Steeg, P. S. et al., 1982). Both the muIFNγ (95–133) (SEQ ID NO. 2) and the huIFNγ (95–134) (SEQ ID NO. 1) peptides produced significant reductions in viral yield as shown in Table 2. None of the other peptides tested, including the muIFNγ (95–133)S (SEQ ID NO. 3) peptide, were able to effect a significant reduction in virus yield. Thus, the peptides of the subject invention possess one of the biological activities of IFNγ.

TABLE 2

IFNγ peptide reduction of VSV yield

| Peptide and concentration | Virus yield (PFU/ml)[a] | Fold reduction |
| --- | --- | --- |
| muIFNγ(95–133) (SEQ ID NO. 2) 100 μM | <10 | >8.0 × 10$^{11}$ |
| muIFNγ(95–133) (SEQ ID NO. 2) 25 μM | 6.0 × 10$^6$ | 1.3 × 10$^6$ |
| huIFNγ(95–134) (SEQ ID NO. 1) 100 μM | 1.0 × 10$^6$ | 8.0 × 10$^6$ |
| huIFNγ(95–134) (SEQ ID NO. 1) 25 μM | 1.0 × 10$^{11}$ | 8.0 |
| muIFNγ(95–133)S* (SEQ ID NO. 3) 100 μM | 1.6 × 10$^{10}$ | 5.0 × 10$^2$ |
| muIFNγ(95–133)S (SEQ ID NO. 3) 25 μM | 6.0 × 10$^{12}$ | 1.3 |
| muIFNγ(95–125) (SEQ ID NO. 4) 100 μM | 4.0 × 10$^{12}$ | 2.0 |
| muIFNγ(1–39) (SEQ ID NO. 5) 100 μM | 8.0 × 10$^{12}$ | 0.0 |
| muIFNγ 200 U/ml (1.3 nM) | 1.2 × 10$^8$ | 6.7 × 10$^4$ |
| muIFNγ 50 U/ml (0.33 nM) | 1.6 × 10$^{10}$ | 5.0 × 10$^2$ |
| Virus control | 8.0 × 10$^{12}$ | — |
| Cell control | 0.0 | — |

[a]P388D$_1$ cells were infected with VSV at a MOI = 0.5, and virus produced was harvested and assayed on L929 cells in a standard yield reduction assay (Weigent, D. A. et al., 1981).
*Denotes a scrambled version of peptide muIFNγ(95–133) (SEQ ID NO. 2).

MuIFNγ (95–133) (SEQ ID NO. 2) showed no antiviral activity on murine L cells due to their lack of phagocytic activity. Also, supernatants from P388D$_1$ cells treated with 100 μM muIFNγ (95–133) (SEQ ID NO. 2) or huIFNγ (95–134) (SEQ ID NO. 1) did not exhibit antiviral activity on L cells. Thus, the antiviral activity of IFNγ C-terminal peptides is due to a direct intracellular effect of the peptides as opposed to the induction of interferon production in these cells.

Figure 1A:
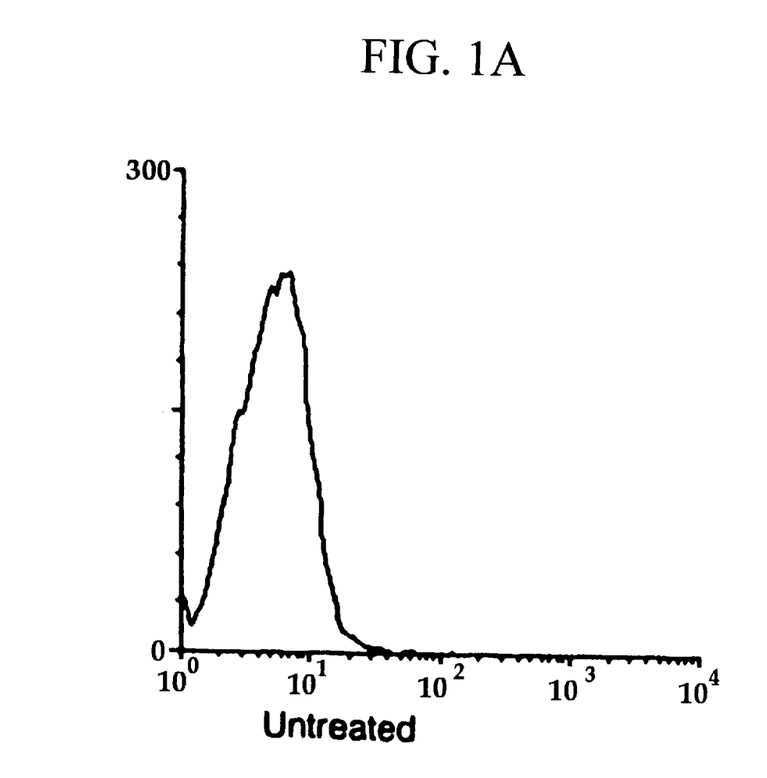
FIGS. 1A–1F show IFNγ C-terminal peptide induction of Ia expression on the murine macrophage line P388D$_1$. Cells were incubated for 24 hours with IFNγ peptides at a final concentration of 100 μM as follows: (1A) medium alone, (1B) muIFNγ (95–133) (SEQ ID NO. 2), (1C) huIFNγ (95–134) (SEQ ID NO. 1), (1D) muIFNγ (95–133)S (SEQ ID NO. 3), (1E) muIFNγ (95–125) (SEQ ID NO. 4), and (1F) muIFNγ (1–39) (SEQ ID NO. 5).
Figure 1B:
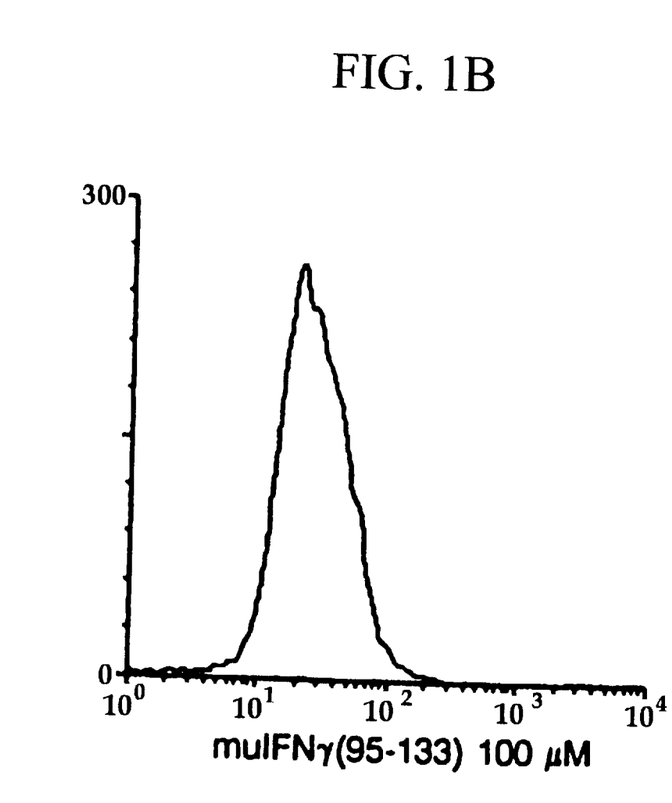
Figure 1C:
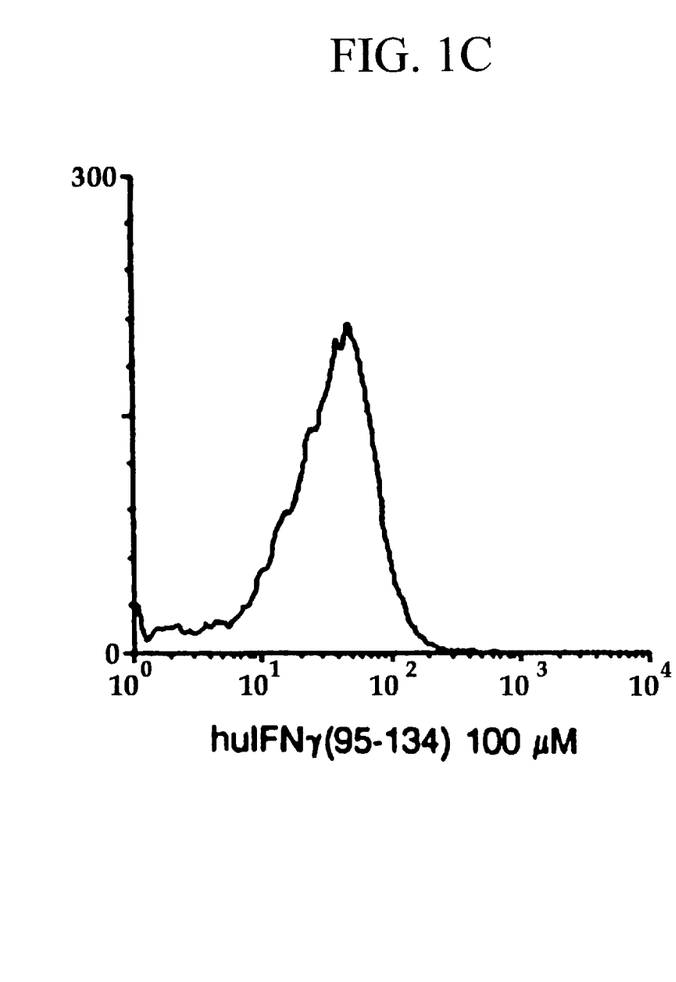
Figure 1D:
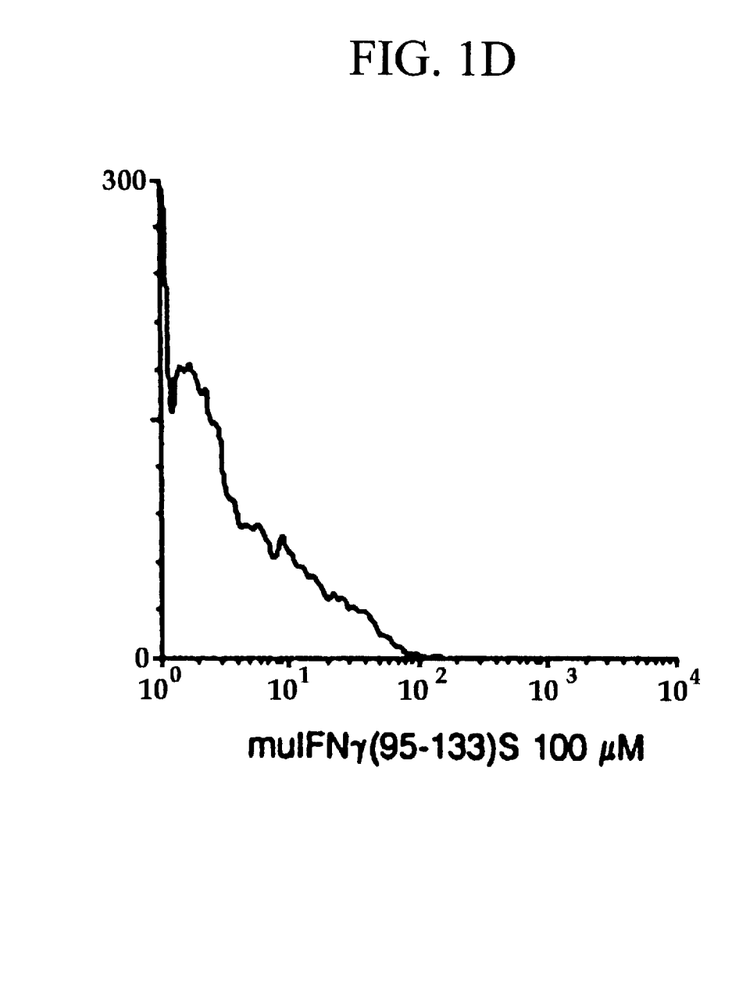
Figure 1E:
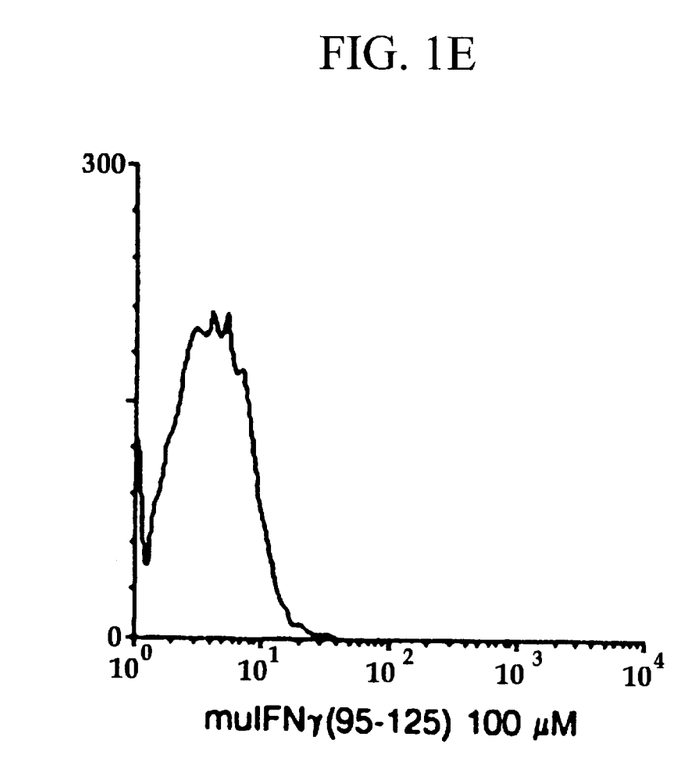
Figure 1F:
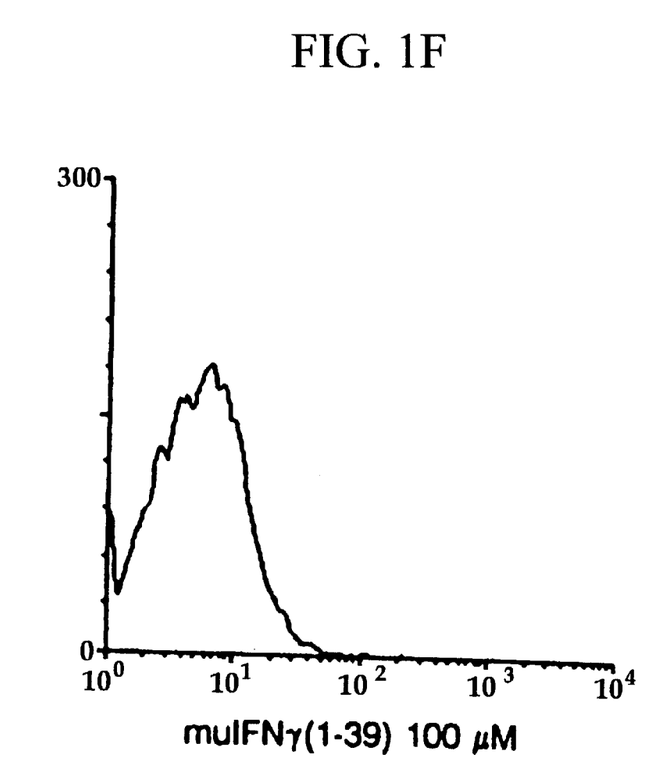

The peptides of the subject invention were also tested for their ability to induce increased MHC class II antigen expression on a target cell. P388D$_1$ cells were treated with the peptides shown in Table 1 and then the level of cell surface Ia antigen (a murine MHC class II antigen) expression was determined by fluorescence-activated cell sorting (FACS) analysis. As shown in FIGS. 1(A)–1(F), cells treated with the muIFNγ (95–133) (SEQ ID NO. 2) or huIFNγ (95–134) (SEQ ID NO. 1) peptides exhibited a ten-fold increase in the level of Ia expression above that of untreated cells. The other peptides tested failed to significantly increase Ia expression on the treated cells. Thus, the peptides of the subject invention, once internalized within the cytoplasm of a cell, exhibit biological activity associated with IFNγ.

The discovery of peptide agonists of IFNγ is highly unexpected. Use of synthetic peptide agonists rather than the full-length IFNγ molecule offers advantages such as targeting of specific cells and immune system components. Also, specific amino acid residues of the peptides can be easily and rapidly modified to allow for generation of more effective agonists or antagonists.

As those skilled in the art can readily appreciate, there can be a number of variant sequences of a protein found in nature, in addition to those variants that can be artificially created by the skilled artisan in the lab. The peptides of the subject invention encompasses those specifically exemplified herein, as well as any natural variants thereof, as well as any variants which can be created artificially, so long as those variants retain the desired biological activity.

The peptides contemplated in the subject invention include the specific peptides exemplified herein as well as equivalent peptides which may be, for example, somewhat longer or shorter than the peptides exemplified herein. For example, using the teachings provided herein, a person skilled in the art could readily make peptides having from 1 to about 15 or more amino acids added to, or removed from, either end of the disclosed peptides using standard techniques known in the art. Preferably, any added amino acids would be the same as the corresponding amino acids of a mature full-length IFNγ protein. The skilled artisan, having the benefit of the teachings disclosed in the subject application, could easily determine whether a variant peptide retained the biological activity of the specific peptides exemplified herein. Such a longer or shorter peptide would be within the scope of the subject invention as long as said peptide does not encompass the entire full-length IFNγ protein and said longer or shorter peptide retains substantially the same relevant biological activity as the peptides exemplified herein. For example, a longer or shorter variant of the huIFNγ (95–134) (SEQ ID NO. 1) peptide would fall within the scope of the subject invention if the variant peptide had the ability to induce MHC class II antigen expression or to increase cellular resistance to viral infection.

Also within the scope of the subject invention are peptides which have the same amino acid sequences of a peptide exemplified herein except for amino acid substitutions, additions, or deletions within the sequence of the peptide, as long as these variant peptides retain substantially the same relevant biological activity as the peptides specifically exemplified herein. For example, conservative amino acid substitutions within a peptide which do not affect the ability of the peptide to, for example, induce the expression of MHC class II molecules would be within the scope of the subject invention. Thus, the peptides disclosed herein should be understood to include variants and fragments, as discussed above, of the specifically exemplified sequences.

The subject invention further includes nucleotide sequences which encode the peptides disclosed herein. These nucleotide sequence can be readily constructed by those skilled in the art having the knowledge of the protein and peptide amino acid sequences which are presented herein. As would be appreciated by one skilled in the art, the degeneracy of the genetic code enables the artisan to construct a variety of nucleotide sequences that encode a particular peptide or protein. The choice of a particular nucleotide sequence could depend, for example, upon the codon usage of a particular expression system.

The subject invention contemplates the use of the peptides described herein in pharmaceutical compositions for administration to an animal or human for the treatment of clinically important disease conditions that are amenable to treatment with full-length IFNγ. For example, using the teachings described herein, the skilled artisan can use the subject invention to modulate or stimulate the immune response of an animal or human. Similarly, the subject peptides can be used to treat certain viral infections, as well as to treat certain forms of cancer or tumors. The peptides of the subject invention can be prepared in pharmaceutically acceptable carriers or diluents for administration to humans or animals in a physiologically tolerable form. Materials and methods for preparing such compositions are known in the art.

The peptides of the subject invention can be administered using a variety of techniques that are known in the art. The peptides can be encapsulated in liposomes that are targeted to specific cells or tissues and the liposome-encapsulated peptides delivered to the cells or tissue either in vivo or ex vivo. Procedures for preparing liposomes and encapsulating compounds within the liposome are well known in the art. See, for example, U.S. Pat. No. 5,252,348, which issued to Schreier et al. Peptides could also be conjugated or attached to other molecules, such as an antibody, that targeted a specific cell or tissue. Peptides could also be administered using a drug delivery system similar to that described in U.S. Pat. No. 4,625,014, which issued to Senter et al.

As described herein, the peptide sequences of the subject invention can also be the basis for producing peptides that act as IFNγ antagonists. These antagonists are also within the scope of the subject invention. Inhibition or antagonism of IFNγ function without agonist activity can be accomplished through the use of anti-peptide antibodies or modification of residues within the peptide itself. An especially productive means for generation of peptide antagonists has been substitution of L-amino acids with D-amino acids. The efficacy of this approach has been well characterized in the generation of arginine vasopressin analogs with selectively enhanced antidiuretic antagonism by appropriate substitution of L-amino acids with D-amino acids (Manning, M. et al., 1985). Further, not only can antagonism be produced with D-amino acid substitutions, but this antagonism can be directed toward a specific function. Production of potent antagonist peptides can be of value in specifically manipulating immune function.

Peptide antagonists to IFNγ can also be derived using those portions of the cytoplasmic domain of the IFNγ receptor which bind to IFNγ protein or the peptides disclosed herein. For example, a peptide comprising amino acid residues 253 through 287 of the murine IFNγ receptor or amino acid residues 252 through 291 of the human IFNγ receptor could be used as IFNγ antagonists. These peptides from the IFNγ receptor have been shown to bind to IFNγ protein and to the huIFNγ (95–134) (SEQ ID NO. 1) and muIFNγ (95–133) (SEQ ID NO. 2) peptides of the subject invention (Szente, B. E. et al., 1994(a); Szente, B. E. et al., 1994(b)).

A further aspect of the claimed invention is the use of the claimed peptides to produce antibodies, both polyclonal and monoclonal. These antibodies can be produced using standard procedures well known to those skilled in the art. These antibodies may be used as diagnostic and therapeutic reagents. For example, antibodies that bind to the huIFNγ (95–134) (SEQ ID NO. 1) peptide may be used as an antagonist to block the function of IFNγ. Antibodies that are reactive with the peptides of the subject invention can also be used to purify the IFNγ protein or peptides from a crude mixture.

The subject peptides can also be used in the design of new drugs that bind to the cytoplasmic domain of the IFNγ receptor. Knowledge of peptide sequences that induce IFNγ biological activity upon binding of the peptide to a localized region on the IFNγ receptor enables a skilled artisan to develop additional bioactive compounds using rational drug design techniques. Thus, the skilled artisan can prepare both agonist and antagonist drugs using the teachings described herein.

Materials and Methods

Synthetic peptides

Peptides corresponding to portions of the IFNγ protein were synthesized with a Biosearch 9500AT automated peptide synthesizer (Milligen/Biosearch, Burlington, Mass.) using 9-fluoroenylmethyl oxycarbonyl chemistry (Chang, C. D. et al., 1978). Peptides were cleaved from the resins using trifluoroacetic acid/ethanedithiol/thioanisole/crystalline phenol/distilled water at a ratio of 80/3/5/7/5. The cleaved peptides were then extracted in ether and ethyl acetate and subsequently dissolved in water and lyophilized. Reverse phase HPLC analysis of the crude peptides revealed one major peak in each profile. Amino acid analysis of the peptides showed that the amino acid composition corresponded closely to theoretical values.

The one-letter symbol for the amino acids used in the sequences shown in the Tables is well known in the art. For convenience, the relationship of the three-letter abbreviation and the one-letter symbol for amino acids is as follows:

| | |
|---|---|
| Ala | A |
| Arg | R |
| Asn | N |
| Asp | D |
| Cys | C |
| Gln | Q |
| Glu | E |
| Gly | G |
| His | H |
| Ile | I |
| Leu | L |
| Lys | K |
| Met | M |
| Phe | F |
| Pro | P |
| Ser | S |
| Thr | T |
| Trp | W |
| Tyr | Y |
| Val | V |

Yield Reduction Assay $5 \times 10^5$ P388D$_1$ cells were incubated with peptides at a concentration of 100 μM in maintenance medium (medium containing 2% serum) for 18 to 24 hours. Cells were then rinsed 3 times with medium containing no peptide. Vesicular stomatitis virus (VSV) was added at a Multiplicity of Infection (MOI) of either 0.1 or 0.5 as indicated for a 45 minute incubation. Cells were again washed 3 times. Fresh maintenance medium was added and the cells were incubated overnight at 37° C. Virus was harvested and titered on L929 cells using a standard yield reduction assay (Weigent, D. A. et al., 1981).

Induction of Ia expression $10^5$ P388D$_1$ cells were incubated for 24 hours with IFNγ peptides under standard culture conditions, all at a final concentration of 100 μM, as follows: (A) medium alone, (B) muIFNγ (95–133) (SEQ ID NO. 2), (C) huIFNγ (95–134) (SEQ ID NO. 1), (D) muIFNγ (95–133)S (SEQ ID NO. 3), (E) muIFNγ (95–125) (SEQ ID NO. 4) and (F) muIFNγ (1–39) (SEQ ID NO. 5). After the time period, the cells were physically dislodged from culture plates, washed with FACS buffer (PBS/0.5% BSA+10 mM NaN$_3$), and incubated with the biotinylated anti-Ia monoclonal antibody MKD6 (12), for 1 hour at 37° C. Cells were then washed and incubated with streptavidin-phycoerythrin (TAGO Inc., Burlingame, Calif.) for 15 minutes at room temperature. FACS Analysis was performed on a FACScan (Becton-Dickinson, Mountain View, Calif.) as 10,000 events per sample.

Following are examples which illustrate procedures, including the best mode, for practicing the invention. These examples should not be construed as limiting. All percentages are by weight and all solvent mixture proportions are by volume unless otherwise noted.

EXAMPLE 1

Reduction of Viral Yield

The peptides of the subject invention were tested to determine whether they could function as agonists of IFNγ biological activity. The ability of endocytosed murine and human C-terminal IFNγ peptides of the subject invention to induce an antiviral response in P388D$_1$ cells was shown using a standard yield reduction assay. The muIFNγ (95–133) peptide (SEQ ID NO. 2) at a concentration of 100 μM reduced virus yield by a factor of greater than $8.0 \times 10^{11}$ (Table 2). At a concentration of 25 μM, the same peptide reduced the virus yield by a factor of $1.3 \times 10^6$. A scrambled version of this peptide, muIFNγ (95–133)S (SEQ ID NO. 3) was more than $10^9$-fold less effective in inhibiting virus yield at a concentration of 100 μM, and had no effect on virus replication at a concentration of 25 μM.

In addition to testing a scrambled version of muIFNγ (95–133) (SEQ ID NO. 2), the effect of a truncated form of the peptide, muIFNγ (95–125) (SEQ ID NO. 4), which lacks the polycationic amino acid sequence RKRKR (SEQ ID NO. 6) was also tested for biological activity. Human IFNγ also has a polycationic sequence, KRKR (SEQ ID NO. 7), in the C-terminus portion of the protein. The RKRKR (SEQ ID NO. 6) sequence has previously been shown to be required for antiviral activity of the IFNγ molecule (Russell, J. K. et al., 1986; Leinikki, P. O. et al., 1987; Seelig, G. F. et al., 1988; Wetzel, R. et al., 1990; Lundell, D. et al., 1991). The muIFNγ (95–125) (SEQ ID NO. 4) peptide did not inhibit virus replication. The N-terminal peptide of murine IFNγ, muIFNγ (1–39) (SEQ ID NO. 5), which binds to the extracellular domain of the murine receptor, was also ineffective in inhibiting virus replication. The human C-terminal peptide, huIFNγ (95–134) (SEQ ID NO. 1), similar to its murine counterpart, produced a significant reduction in virus yield ($8.0 \times 10^6$ fold at 100 μM). Murine IFNγ at 1.3 nM final concentration inhibited virus yield by approximately $7.0 \times 10^4$ fold on P388D$_1$ cells. Human IFNγ at a similar concentration had no effect.

EXAMPLE 2

Induction of MHC Class II Expression

A second parameter of the agonist properties of the IFNγ peptides of the subject invention is their ability to increase the level of expression of MHC class II molecules on cells. As shown in FIGS. 1(A)–1(F), treatment of the P388D$_1$ cell line with either the muIFNγ (95–133) (SEQ ID NO. 2) or huIFNγ (95–134) (SEQ ID NO. 1) peptide resulted in an increase in Ia expression tenfold greater than that of untreated cells. This effect is specific to the IFNγ C-terminal peptides with the intact polycationic region (RKRKR or KRKR), as cells treated with either the truncated version of the murine C-terminal peptide, muIFNγ (95–125) (SEQ ID NO. 4), or the scrambled version, muIFNγ (95–133)S (SEQ ID NO. 3), failed to upregulate Ia expression. Similar effects of C-terminal IFNγ peptides of the subject invention were observed using WEHI-3 cells. The time course of induction of Ia expression by the subject peptides is more rapid than that induced by intact IFNγ, with optimal results being achieved by 24 hours. Whereas Ia levels are significantly increased within 24 hours of treatment with 100 μM IFNγ C-terminal peptide, IFNγ itself requires 2 to 3 days to induce similar expression (Steeg, P. S. et al., 1982). This is most likely due to the time required for receptor-dependent internalization and intracellular processing of the intact IFNγ. The peptides of the subject invention are delivered, in effect, already processed, and are taken up via a receptor-independent endocytic mechanism. Thus, the C-terminal peptides of murine and human IFNγ are potent modulators not only of antiviral responses, but also of MHC class II molecule expression.

It should be understood that the examples and embodiments described herein are for illustrative purposes only and that various modifications or changes in light thereof will be suggested to persons skilled in the art and are to be included within the spirit and purview of this application and the scope of the appended claims. All references to publications and patents cited herein are hereby incorporated by reference.

References

Chang, C. D., J. Meienhofer (1978) *Int. J. Pept. Protein Res.* 11:246.

Fairchild, R. L., J. W. Moorhead (1985) *J. Immunol. Meth.* 85:183–193.

Farrar, M. A., R. D. Schreiber (1993) *Annu. Rev. Immunol* 11:571–611.

Gray, P. W., D. V. Goeddel (1983) *Proc. Natl. Acad. Sci. USA* 80:5842–5846.

Griggs, N. D. et al. (1992) *J. Immunol.* 149:517–520.

Johnson, H. M. (1985) *Lymphokines* 11:33.

Leinikki, P. O., J. Calderon, M. H. Luquette, R. D. Schreiber (1987) *J. immunol.* 139:3360–3366.

Lundell, D. et al. (1991) *Prot. Eng.* 4:335–341.

Magazine, H. I. et al. (1988) *Proc. Natl. Acad. Sci. USA* 85:1237–1241.

Manning, M., W. H. Sawyer (1985) *Vasopressin*, pages 131–144.

Pestka, S. J. A. Langer, K. C. Zoon, C. E. Samuel (1987) *Ann. Rev. Biochem.* 56:727.

Rinderknecht, E., B. H. O'Connor, H. Rodriguez (1984) *The Journal of Biological Chemistry* 259(11):6790–6797.

Russell, J. K. et al. (1986) *J. Immunol.* 136:3324–3328.

Sanéau, J., P. Sondermeyer, F. Béranger, R. Falcoff, C. Vaquero (1987) *C. Proc. Natl. Acad. Sci. USA* 84:2906–2910.

Schreier, H., R. Chander, A. A. Stecenko, U.S. Pat. No. 5,252,348, issued Oct. 12, 1993.

Seelig, G. F., J. Wijdenes, T. L. Nagabhushan, P. P. Trotta (1988) *P. P. Biochemistry* 27:1981–1987.

Senter, P. D., J. M. Lambert, W. A. Blattler, U.S. Pat. No. 4,625,014, issued Nov. 25, 1986.

Smith, M. R. et al. (1990) *J. Immunol.* 144:1777–1782.

Steeg, P. S., R. N. Moore, H. M. Johnson, J. J. Oppenheim (1982) *J. Exp. Med.* 156:1780–1793.

Szente, B. E., H. M. Johnson (1994a) *Biochem. Biophys. Res. Commun.* 201:215–221.

Szente, B. E., H. M. Johnson (1994b) *Biochem. Biophys. Res. Commun.* 201:215–221.

VanVolkenburg, M. A. et al. (1993) *J. Immunol.* 151:6206–6213.

Weigent, D. A., G. J. Stanton, M. P. Langford, R. E. Lloyd, S. Baron (1981) Methods Enzymol. 78:346–351.

Wetzel, R., L. J. Perry, C. Veilleuz, G. Chang (1990) *Prot. Eng.* 3:611–623.

Zoltnik, A., R. P. Shimonkevitz, M. L. Gefter, J. Kappler, P. Marrack (1983) *J. Immunol.* 131:2814–2820.

---

We claim:

1. A peptide having an amino acid sequence consisting of the following components:
   optionally, an N-terminal amino acid residue or sequence of residues of from 2 to about 15 amino acids;
   the sequence of a fragment of a mammalian interferon-gamma protein other than murine interferon-gamma, the fragment having about induces MHC class II antigen expression on a target cell, and wherein a peptide having only the amino acid sequence of said fragment binds to the cytoplasmic domain of the interferon-gamma receptor, induces antiviral activity, or induces MHC class II antigen expression on a target cell.

17. The composition according to claim 16, wherein said fragment consists of an amino acid sequence from about amino residue 95 to about amino acid residue 134 of human interferon-gamma, and wherein said N- and C-terminal amino acid residues are the same as the amino acid residues immediately adjacent to said fragment within the sequence of human interferon-gamma.

18. The composition according to claim 16, wherein said fragment consists of an amino acid sequence from about amino residue 95 to about amino acid residue 133 of murine interferon-gamma, and wherein said N- and C-terminal amino acid residues are the same as the amino acid residues immediately adjacent to said fragment within the sequence of murine interferon-gamma.

19. The composition according to claim 16, wherein the peptide consists of an amino acid sequence selected from the group consisting of the amino acid sequences shown as SEQ ID NO: 1 and SEQ ID NO: 2.

\* \* \* \* \*

UNITED STATES PATENT AND TRADEMARK OFFICE
CERTIFICATE OF CORRECTION

PATENT NO. : 5,770,191
DATED : June 23, 1998
INVENTOR(S) : Howard M. Johnson, et al It is certified that error appears in the above-identified patent and that said Letters Patent is hereby corrected as shown below:

Column 4, line 32: "100,$\mu$M" should read --100 $\mu$M--.

Column 9, line 18: "*Immunol*" should read -- *Immunol.*--.

Column 10, line 6: "Saneau," should read --Sancéau,--.

line 27: "C. Veilleuz," should read --C. Veilleux,--.

line 29: "Zoltnik," should read --Zlotnik,--.

Signed and Sealed this

Sixth Day of October, 1998

Attest:

BRUCE LEHMAN

*Attesting Officer*      Commissioner of Patents and Trademarks

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Leu Thr Asn Tyr Ser Val Thr Asp Leu Asn Val Gln Arg Lys Ala Ile
1               5                   10                  15

His Glu Leu Ile Gln Val Met Ala Glu Leu Ser Pro Ala Ala Lys Thr
                20                  25                  30

Gly Lys Arg Lys Arg Ser Gln Met
                35                  40
```

( 2 ) INFORMATION FOR SEQ ID NO:2:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

-continued

```
Ala  Lys  Phe  Glu  Val  Asn  Asn  Pro  Gln  Val  Gln  Arg  Gln  Ala  Phe  Asn
1                   5                        10                       15

Glu  Leu  Ile  Arg  Val  Val  His  Gln  Leu  Leu  Pro  Glu  Ser  Ser  Leu  Arg
               20                       25                       30

Lys  Arg  Lys  Arg  Ser  Arg  Cys
               35
```

(2) INFORMATION FOR SEQ ID NO:3:

(i) SEQUENCE CHARACTERISTICS:
        (A) LENGTH: 39 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:3:

```
Pro  Ser  Cys  Arg  Glu  Asn  Gln  Asn  Ala  Val  Lys  Ile  Gln  Lys  Leu  Ser
1                   5                        10                       15

Val  Val  Leu  Arg  Arg  Glu  Gln  Lys  His  Arg  Val  Glu  Arg  Leu  Ala  Phe
               20                       25                       30

Arg  Asn  Gln  Ser  Leu  Pro  Phe
               35
```

(2) INFORMATION FOR SEQ ID NO:4:

(i) SEQUENCE CHARACTERISTICS:
        (A) LENGTH: 31 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:4:

```
Ala  Lys  Phe  Glu  Val  Asn  Asn  Pro  Gln  Val  Gln  Arg  Gln  Ala  Phe  Asn
1                   5                        10                       15

Glu  Leu  Ile  Arg  Val  Val  His  Gln  Leu  Leu  Pro  Glu  Ser  Ser  Leu
               20                       25                       30
```

(2) INFORMATION FOR SEQ ID NO:5:

(i) SEQUENCE CHARACTERISTICS:
        (A) LENGTH: 39 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:5:

```
His  Gly  Thr  Val  Ile  Glu  Ser  Leu  Glu  Ser  Leu  Asn  Asn  Tyr  Phe  Asn
1                   5                        10                       15

Ser  Ser  Gly  Ile  Asp  Val  Glu  Glu  Lys  Ser  Leu  Phe  Leu  Asp  Ile  Trp
               20                       25                       30

Arg  Asn  Trp  Gln  Lys  Asp  Gly
               35
```

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:6:

Arg Lys Arg Lys Arg
1               5

(2) INFORMATION FOR SEQ ID NO:7:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:7:

Arg Lys Arg Lys
1

(2) INFORMATION FOR SEQ ID NO:8:

(i) SEQUENCE CHARACTERISTICS:
(A) LENGTH: 143 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:8:

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Arg Ala Ser Gln
    130                 135                 140

(2) INFORMATION FOR SEQ ID NO:9:

(i) SEQUENCE CHARACTERISTICS:
(A) LENGTH: 133 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:9:

His Gly Thr Val Ile Glu Ser Leu Glu Ser Leu Asn Asn Tyr Phe Asn
1               5                   10                  15

-continued

```
Ser    Ser    Gly    Ile    Asp    Val    Glu    Glu    Lys    Ser    Leu    Phe    Leu    Asp    Ile    Trp
                     20                                 25                                 30

Arg    Asn    Trp    Gln    Lys    Asp    Gly    Asp    Met    Lys    Ile    Leu    Gln    Ser    Gln    Ile
              35                          40                                 45

Ile    Ser    Phe    Tyr    Leu    Arg    Leu    Phe    Glu    Val    Leu    Lys    Asp    Asn    Gln    Ala
       50                          55                                 60

Ile    Ser    Asn    Asn    Ile    Ser    Val    Ile    Glu    Ser    His    Leu    Ile    Thr    Thr    Phe
65                          70                                 75                                        80

Phe    Ser    Asn    Ser    Lys    Ala    Lys    Lys    Asp    Ala    Phe    Met    Ser    Ile    Ala    Lys
                     85                                 90                                        95

Phe    Glu    Val    Asn    Asn    Pro    Gln    Val    Gln    Arg    Gln    Ala    Phe    Asn    Glu    Leu
                     100                                105                                110

Ile    Arg    Val    Val    His    Gln    Leu    Leu    Pro    Glu    Ser    Ser    Leu    Arg    Lys    Arg
              115                          120                                125

Lys    Arg    Ser    Arg    Cys
       130
```